United States Patent [19]

Alberti et al.

[11] Patent Number: 5,344,548
[45] Date of Patent: Sep. 6, 1994

[54] SOLID STATE SENSOR DEVICE FOR THE DETERMINATION OF THE CONCENTRATION OF GASES WHICH CAN REACT WITH HYDROGEN

[75] Inventors: Giulio Alberti; Roberto Palombari, both of Perugia, Italy

[73] Assignee: Eniricerche S.p.A., San Donato Milanese, Italy

[21] Appl. No.: 71,364

[22] Filed: Jun. 3, 1993

Related U.S. Application Data

[63] Continuation of Ser. No. 810,510, Dec. 19, 1991, abandoned.

[30] Foreign Application Priority Data

Dec. 21, 1990 [IT] Italy ................. 22485 A/90

[51] Int. Cl.$^5$ ............................. G01N 27/407
[52] U.S. Cl. ......................... 204/424; 204/426
[58] Field of Search ............. 204/153.18, 421–429

[56] References Cited

U.S. PATENT DOCUMENTS 4,560,444 12/1985 Polak et al. ............... 204/426
4,661,211 4/1987 Petty-Weeks ............... 204/424
4,795,533 1/1989 Young ...................... 204/421

FOREIGN PATENT DOCUMENTS 0206969 12/1986 European Pat. Off. .
0330248 8/1989 European Pat. Off. .
0432840 6/1991 European Pat. Off. .

OTHER PUBLICATIONS

K. Otsubo, K. Kawamura, J. Inanaga, and M. Yamaguchi, Chemistry Letters, pp. 1487–1490, 1987 (The Chemical Society of Japan).
S. Kuwata, N. Miura and N. Yamazoe, Chemistry Letters, pp. 1197, 1200 (1988) (The Chemical Society of Japan).
T. Inoue K. Eguchi and H. Arai, Chemistry Letters, pp. 1939–1942 (1988) (The Chemical Society of Japan).

*Primary Examiner*—T. Tung
*Attorney, Agent, or Firm*—George P. Hoare, Jr.

[57] ABSTRACT

A solid-state sensor device for determining the concentration of gases which can react with hydrogen, in particular oxygen, is disclosed, which is essentially composed of a solid-state protonic conductor put into contact, at one of its sides, with a reference electrode and, at its other side, with a composite electrode (sensor electrode), constituted by a catalytic material into contact with a hydride of a metal or of a metal alloy.

8 Claims, 3 Drawing Sheets

SOLID STATE SENSOR DEVICE FOR THE DETERMINATION OF THE CONCENTRATION OF GASES WHICH CAN REACT WITH HYDROGEN

This application is a continuation of application Ser. No. 810,510 filed Dec. 19, 1991 (now abandoned).

BACKGROUND OF THE INVENTION

The present invention relates to a solid-state sensor device for determining the concentration of gas species, in particular oxygen, which sensor device is capable of operating also at room temperature.

The determination of oxygen content in a gas mixture, or in liquids, is a very important problem, from the industrial, biological, environmental, and still other, viewpoints.

Very often, a continuous monitoring is required, as in the case of rivers, lakes, or seas, in order to keep controlled the level of pollution by organic materials. Such a need may arise also in the case of biological liquids in general, or when dealing with gases generated by combustion processes, and so forth.

For such purposes, sensor devices of voltammetric type are normally used [see: L. C. Clark, Jr., Trans. Am. Soc. Artif. Intern. Organs 2, 41 (1956)].

During the past ten years, also potentiometric systems were introduced, which make use of a solid $O_2$ conductor, usually yttrium-doped zirconia. Unfortunately, all such potentiometric systems have high operating temperatures, higher than 300°–400° C. [see: E. Siebert, J. Fouletier, S. Vilminot "Solid State Ionics", 9& 10 (1983) 1291].

Very recently, attempts were carried out aiming at decreasing the operating temperatures of the potentiometric sensor devices, by studying different types of solid electrolytes [see: Miura, J. Hisamoto. S. Kuwata, N. Yamazoe, "Chemistry Letters" (1987) 1477; T. Inoue, K. Eguchi, H. Arai "Chemistry Letters" (1988), 1939; S. Kuwata, N. Miura, Y. Yamazoe, "Chemistry Letters" (1988), 1197].

Recently, the same Applicant developed a potentiometric sensor device for oxygen, operating at room temperature, claimed in European Patent Application Public. No. 0 432 840, in order to determine the concentration of gases which can react with hydrogen, in particular oxygen, which sensor device is essentially constituted by a solid-state protonic conductor kept into contact, at one of its sides, with a reference electrode—constituted, in its turn, by a hydride of a metal or metal alloy—and, at its other side, with an electrode which catalyzes the reaction of the gas to be detected, with hydrogen.

Such a sensor device is based on the measurement of the mixed potential which is generated on the catalytic electrode in the presence of oxygen and hydrogen.

In such a sensor device, hydrogen is produced by current or potentiostatic impulses, and the potential is measured after a suitable time interval between each impulse and the subsequent impulse.

The sensor device according to the above cited patent application resulted to respond to up to a few parts of oxygen per million parts (ppm).

SUMMARY OF THE INVENTION

The present Applicant has surprisingly found now a new type of potentiometric sensor device for oxygen, which sensor device is capable of also operating at room temperatures, and does not need hydrogen to be produced by impulses of electric current fed to the catalytic electrode,

BRIEF DESCRIPTION OF THE DRAWINGS

The accompanying drawings, which are incorporated in and constitute a part of this specification, illustrate a preferred embodiment of the invention and, together with the description, serve to explain the principles of the invention.

DETAILED DESCRIPTION OF THE PREFERRED EMBODIMENTS

Figure 1:
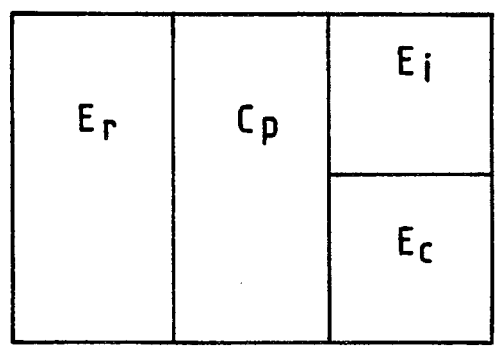
FIG. 1 is a schematic illustration of the sensor device according to the present invention.

Reference will now be made in detail to the present preferred embodiments of the invention, examples of which are illustrated in the accompanying drawings in which like reference characters refer to corresponding elements.

The solid-state sensor device which is the subject-matter of the present invention, for determining the concentration of gases which can react with hydrogen, in particular oxygen, is essentially composed of a protonic conductor kept in contact, at one of its sides, with a reference electrode (which supplies a constant reference potential) and, at its other side, with a composite electrode (sensor electrode), constituted by a catalytic material, preferably platinum or palladium, kept into contact with a hydride of a metal or metal alloy.

Such a hydride, which secures a constant activity of $H_2$ on the catalyst and which can be of interstitial type, intermetallic type, or of other types, either stoichiometric or not, is preferably selected from among titanium hydrides (e.g., $TiH_x$, $TiH_2$, $TiNiH_3$), zirconium hydrides $ZrH_x$, $ZrH_2$, $ZrNiH_3$) and niobium hydrides (NbH).

As the protonic conductor, one already known from literature can be used, such as uranyl hydrogen phosphate, antimonic acid, phosphomolybdic acid, zirconium hydrogen phosphate, zirconium triphosphate and its silicate-doped forms, such as $H_3Zr_2PO_4(SiO_4)_2$, organic polymers containing acidic groups, such as —COOH, —$SO_3$ (e.g., NAFION or IONAC membranes).

Zirconium hydrogen phosphate can be preferably used as a film or as a pre-fabricated membrane, as disclosed in European Patent Application Public No. 0 330 248.

The reference electrode can be coated with such films or pre-fabricated membranes according to the procedure as disclosed in the above said prior patent application.

Inasmuch as very thin, dense films (<0.1 mm) can be obtained, the electrical resistance of the system results to be appreciably reduced. Furthermore, such a protonic conductor is very suitable for uses at room temperatures, as well as at higher temperatures, up to a maximum of 350°–450° C., above which the condensation of —P—OH acidic groups to yield pyrophosphate takes place.

As reference electrodes, hydrides of metals or metal alloys with a low $H_2$ pressure, such as $TiH_x$ or $TiH_2$, can be used.

The preparation of the reference electrode of titanium hydride can be carried out, e.g., by heating at temperatures comprised within the range of from 400° to 700° C. and for 2–10 hours, a titanium plate (having a thickness of 0.25–1.0 mm), in the presence of hydrogen gas, as disclosed in European Patent Appln. Public. No. 0 330 248; or it can be carried out by electrolytic route. According to still another procedure, a pellet of $TiH_2$, using commercial $TiH_2$, can be used.

The electrode which responds to the change in oxygen pressure (i.e., the sensor is a electrode) is a composite electrode, constituted by a material which catalyzes the reaction of the gas to be analyzed with hydrogen, kept into contact with a metal hydride which secures a constant hydrogen activity on the catalyst.

Such an electrode can be prepared, e.g., by starting from a surface-hydrided Zr plate, hydrided either with hydrogen gas at temperatures comprised within the range of from 400° C. to 700° C., or by electrolysis, or by chemical attack with HF at 10% concentration.

The hydrided surface is then partially coated with a layer of Pt or Pd deposited by sputtering.

Such a deposited layer should cover only a portion of the surface.

According to another route, a powder of stoichiometric hydride can be used, which is available from the market in fine powder form. In that case, the electrode can be obtained as a pellet, or, possibly, can be mixed with a suitable conductive paint. The catalytic material can be placed above the powder, as a net, or as a spiral-wound wire, before pressing. In that way, a pellet is obtained, onto the surface of which the catalytic material is applied.

To obtain a thin pellet, a thin disk of an inert metal, such as, e.g., Ag, as the support for the powder, is preferably used.

The Applicant found that the potential "E", measured at the electrodes of such a system, changes as a function of the partial pressure of oxygen, $P_{O2}$, according to the following equation:

$$E = A + B \log P_{O2}$$

The constant "A" depends on the type of hydride used for the reference electrode, as well as for the sensor electrode, whilst the constant "B" is influenced, besides such geometrical factors as the surface area of the catalytic material, also by relative humidity.

In FIG. 1 a sensor device according to the present invention is schematically shown, in which:
$E_r$ = reference electrode;
$C_p$ = protonic conductor;
$E_i + E_c$ = sensor electrode, in which:
  $E_c$ = part of sensor electrode constituted by the catalytic material
  $E_i$ = part of sensor electrode constituted by a metal hydride.

Some examples are given now in order to better illustrate the invention, it being anyway understood that in no way shall the invention be regarded as limited to them or by them.

EXAMPLE 1

A sensor device, constituted by $TiH_x$ hydrided at 650° C. with hydrogen, as the reference electrode, by a membrane of film-shaped zirconium phosphate as the solid, protonic-conduction electrolyte and a zirconium plate hydrided at 650° C. with hydrogen, and platinum-coated by sputtering on approximately 10% of its surface area, was used in order to measure the oxygen content in air-nitrogen mixtures at room temperature with relative humidity close to 100%.

Figure 2:
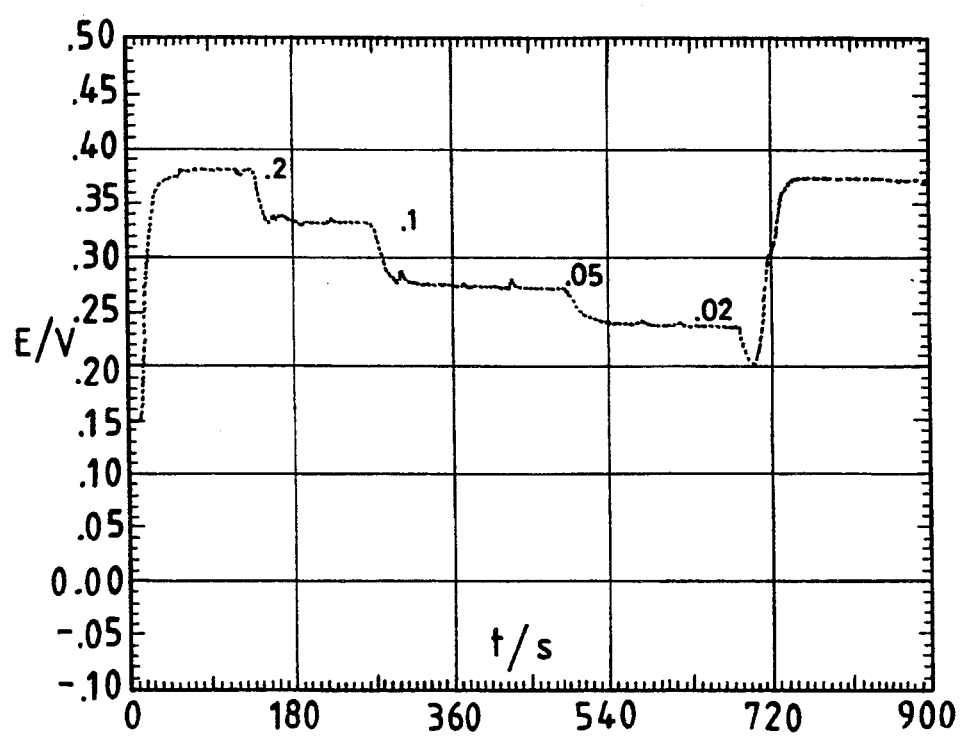
FIG. 2 illustrates the response over time of the sensor device configured in accordance with Example 1.

In FIG. 2, the response of the sensor device over time, with variable $O_2$ partial pressures (indicated on the figure), is reported in chart form.

EXAMPLE 2

A sensor device according to Example 1 was calibrated at 80° C. For that purpose, a system of exponential dilution was used: oxygen initially contained at partial pressure $P^0$ inside a known volume V, is diluted by means of a constant nitrogen flow "F". From the container, oxygen leaves with a partial pressure P, which depends on time t according to the equation:

$$\ln P = \ln P^0 - Ft/V$$

Inasmuch as the potential supplied by the sensor device is bound to the concentration of $O_2$ by a logarithmic relationship, one should expect a linear behaviour of potential as a function of time.

Figure 3:
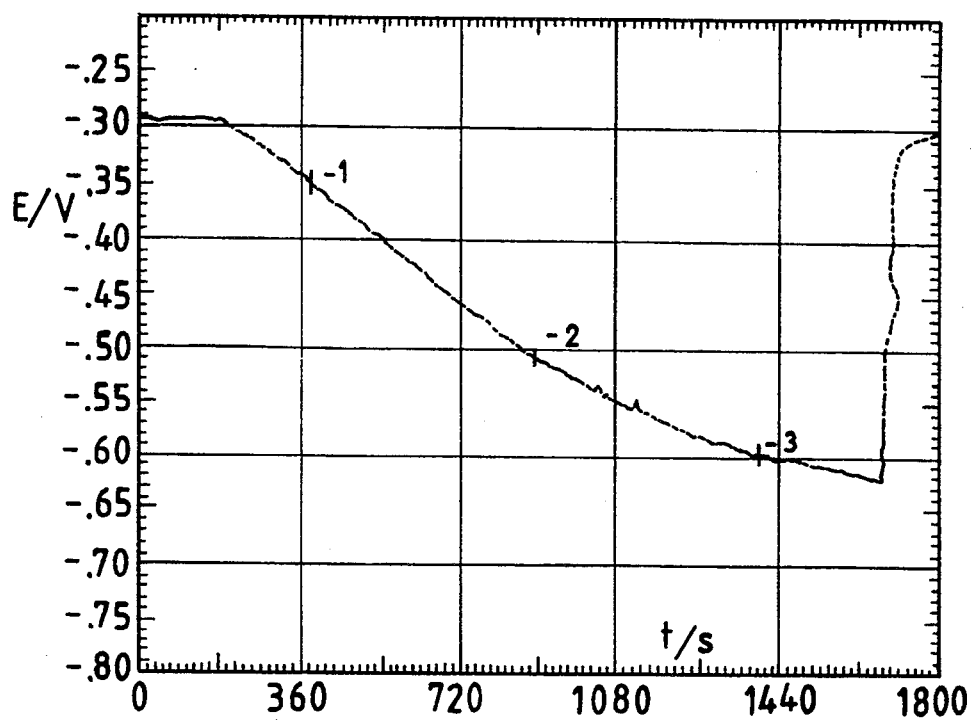
FIG. 3 illustrates the response over time of the sensor device configured in accordance with Example 2.

In FIG. 3, the response is shown of the sensor device as a function of time, and at different values of $O_2$ partial pressure (the numerical values reported on the figure are the logarithm of oxygen partial pressure).

EXAMPLE 3

A sensor device identical to the one disclosed in Example 1, but for the protonic conductor, which consisted of an organic sulfonate membrane (Ionac 3235 MC in H-form) and for the sensor electrode, which was constituted by a zirconium plate hydrided by chemical attack with HF and platinum-coated on approximately 30% of its surface area, was calibrated by mixing air and nitrogen, by an exponential dilution method.

Figure 4:
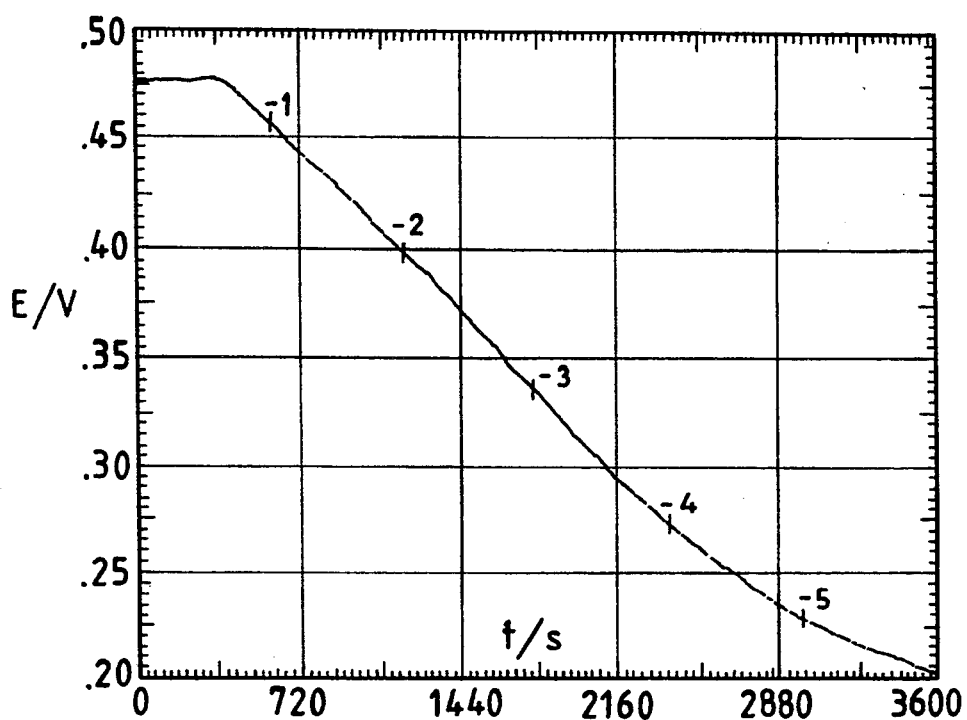
FIG. 4 illustrates the response over time of the sensor device configured in accordance with Example 3.

In FIG. 4, the response is shown, which is displayed by the sensor device as a function of time, and of $O_2$ pressure (the numerical values reported on the figure are the logarithm of oxygen partial pressure).

EXAMPLE 4

Figure 5:
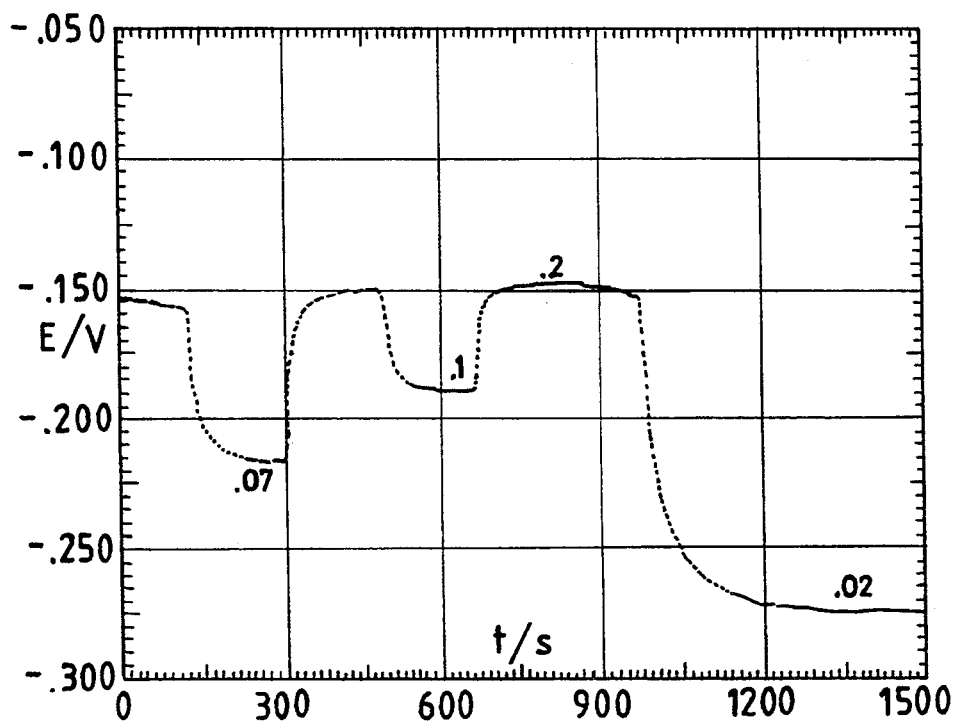
FIG. 5 illustrates the response over time of the sensor device configured in accordance with Example 4.

A sensor device which was identical to the sensor device of Example 1, but as regards the sensor element, which was constituted by a pellet of 10 mm of diameter obtained from $ZrH_2$ powder on which, before the pressing step, a net made from thin Pt wire (surface area = about 10 mm²) was laid, was used to measure the oxygen content in air-nitrogen mixtures, at room temperature, with a relative humidity close to 100%. The response of the sensor device as a function of oxygen partial pressure is reported in FIG. 5.

We claim:
1. A solid-state sensor device for determining the concentration of a gas which can react with hydrogen and consisting essentially of:
  (a) a protonic conductor having first and second sides;
  (b) a first reference electrode in contact with said protonic conductor on the first side thereof, said reference electrode being a metal hydride or metal alloy hydride which provides a constant reference potential; and (c) a second sensor electrode in contact with said protonic conductor on the second side thereof, said sensor electrode being a composite of (i) a material which catalyzes the reaction of the gas to be determined with hydrogen and, in contact therewith, (ii) a metal hydride or a metal alloy hydride.

2. Sensor device according to claim 1, wherein the metal hydride of the sensor electrode is zirconium hydride.

3. Sensor device according to claim 1, wherein the metal hydride of the sensor electrode is titanium hydride.

4. Sensor device according to claim 1, wherein the metal hydride of the sensor electrode is niobium hydride.

5. Sensor device according to claim 1, wherein the protonic conductor is selected from the group consisting of uranyl hydrogen phosphate, antimonic acid, phosphomolybdic acid, zirconium hydrogen phosphate, organic polymers containing acidic groups, and zirconium triphosphate and its silicate-doped forms.

6. Sensor device according to claim 5, wherein the protonic conductor is zirconium hydrogen phosphate in the form of a film coated on a substrate, or in the form of a pre-fabricated membrane.

7. Sensor device according to claim 1, wherein the reference electrode is of titanium hydride.

8. Sensor device according to claim 1, wherein the catalytic material is selected from the group consisting of platinum and palladium.

* * * * *